United States Patent [19]

Lee et al.

[11] Patent Number: 4,511,498
[45] Date of Patent: Apr. 16, 1985

[54] MIXED PHENYL/MESITYL PHOSPHATE ESTER COMPOSITION

[75] Inventors: Fui-Tseng H. Lee, Princeton; Charles V. Juelke, Belle Mead; Joseph H. Finley, Metuchen, all of N.J.

[73] Assignee: FMC Corporation, Philadelphia, Pa.

[21] Appl. No.: 557,706

[22] Filed: Dec. 2, 1983

Related U.S. Application Data

[62] Division of Ser. No. 348,636, Feb. 16, 1982, Pat. No. 4,446,062.

[51] Int. Cl.$^3$ .............................................. C09K 3/28
[52] U.S. Cl. .................................... 252/609; 252/601
[58] Field of Search ................................ 252/601, 609

[56] References Cited

U.S. PATENT DOCUMENTS

| | | | |
|---|---|---|---|
| 3,429,850 | 2/1969 | Holoch | 260/45.9 |
| 3,526,679 | 9/1970 | Strauss et al. | 260/887 |
| 3,639,506 | 2/1972 | Haaf | 260/874 |
| 3,663,654 | 5/1972 | Haaf | 260/874 |
| 3,809,729 | 5/1974 | Reinhard | 260/874 |
| 3,816,562 | 6/1974 | Holoch et al. | 260/874 |
| 3,859,395 | 1/1975 | Terhune et al. | 260/966 |
| 3,883,613 | 5/1975 | Cooper | 260/874 |
| 3,931,091 | 1/1976 | de Radzitzky d'Ostrowick | 260/30.6 R |
| 3,960,808 | 6/1976 | Katchman | 260/42.18 |
| 3,981,841 | 9/1976 | Abolins | 260/42.18 |
| 4,020,124 | 4/1977 | Abolins | 260/876 R |
| 4,101,504 | 7/1978 | Cooper | 260/42.18 |
| 4,123,475 | 10/1978 | Abolins | 260/874 |
| 4,131,598 | 12/1978 | Abolins | 260/42.18 |
| 4,139,487 | 2/1979 | Garrett | 252/182 |
| 4,196,116 | 4/1980 | Haaf et al. | 260/42.18 |
| 4,198,492 | 4/1980 | Izawa et al. | 525/134 |

FOREIGN PATENT DOCUMENTS

| | | |
|---|---|---|
| 86760 | 8/1983 | European Pat. Off. |
| 2485027 | 12/1981 | France |
| 2027712 | 2/1980 | United Kingdom |
| 2078226 | 1/1982 | United Kingdom |

*Primary Examiner*—Richard D. Lovering
*Assistant Examiner*—Catherine S. Kilby
*Attorney, Agent, or Firm*—Robert D. Jackson; Eugene G. Horsky; Eugene G. Seems

[57] ABSTRACT

A mixed phenyl/mesityl phosphate ester composition that is useful as a fire retardant additive, having a phosphorus content of from about 8.2% to about 8.4% is prepared by reacting with agitation at about 120° C. to 130° C. distilled still bottom phenols with phosphorus oxychloride in the presence of a Friedel-Crafts catalyst to form a reaction product containing a substantial quantity of monoaryl phosphodichloridate and diaryl phosphochloridate. This reaction product is then further reacted at an elevated temperature with sufficient phenol to form a triaryl phosphate ester mixture. The mixed phenyl/mesityl phosphate ester so obtained remains a liquid at room temperature over a substantial period of time.

2 Claims, No Drawings

MIXED PHENYL/MESITYL PHOSPHATE ESTER COMPOSITION

This application is a division of application Ser. No. 348,636, filed 2/16/82 now U.S. Pat. No. 4,446,062.

The present invention relates to a mixed phenyl/mesityl phosphate ester prepared from still bottom phenols.

In the manufacture of 2,6-dimethylphenol by the alkylation of phenol, a substantial amount of mesitol and other isomers of 2,6-dimethylphenol is formed as a by-product. This by-product, which remains after separation of the desired 2,6-dimethylphenol, may be distilled and the distillate reacted with phosphorus oxychloride in the presence of a Friedel-Crafts catalyst to form an intermediate mixture of monomesityl phosphodichloridate and dimesityl phosphochloridate. Subsequent reaction of this reaction product with additional phenol gives an ester mixture that can be separated from the catalyst and any unreacted phenols by distillation. The mesityl phenyl phosphate ester mixture is liquid at room temperature, and although small crystals may separate from solution upon standing, the mixed ester may readily be transferred at room temperature by pumping.

Trimesityl phosphate is a well-known phosphate ester which melts at 105° C. to 108° C. Use of trimesityl phosphate as a flame retardant additive for polyphenylene ether-styrene resin compositions is described in U.S. Pat. No. 3,883,613.

Triphenyl phosphate is also known to be a useful flame retardant additive. This product is also a solid at room temperature, melting at 49° C. to 51° C. Both monophenyl dimesityl phosphate and monomesityl diphenyl phosphate are also solids at room temperature.

Mono- and dimesityl isopropylphenyl phosphate esters are disclosed in British Patent Application No. 2027712. Such triaryl phosphates are liquid at room temperature and are said to be useful as flame retardant additives for thermoplastic or thermosetting resins.

In accordance with the present invention, a novel mixed phosphate ester additive composition that is useful as a fire retardant comprising about 20 weight percent triphenyl phosphate, about 40 weight percent diphenyl mesityl phosphate and about 40 weight percent phenyl dimesityl phosphate is prepared that is a liquid at room temperature and has a viscosity at 65.6° C. in the range of about 0.000018–0.000024 meter$^2$ per second (18–24 centistokes). The mixed phosphate ester compositions of the present invention contain from about 8.2% to about 8.4% phosphorus and may be prepared by heating and stirring from about 1.02 to about 1.23 moles of distilled still bottom phenols containing more than about 95 weight percent of mesitol, no more than about 2 weight percent 2,4-xylenol and no more than about 0.5 weight percent of total ortho monosubstituted phenol isomers; with about 1 mole of phosphorus oxychloride in the presence of a Friedel-Crafts catalyst at 120° C. to 130° C. until the amount of unreacted mesitol is less than 1 weight percent. From about 1.9 to about 2.12 moles of phenol are then added to the reaction mixture with stirring while maintaining the temperature of the reaction mixture at 120° C. to 130° C. After addition of the phenol, the reaction mixture is heated to about 220° C. and stirring is continued at that temperature for sufficient time to form the desired mixed phosphoric acid ester composition. The mixed phosphoric ester product may be recovered by vacuum distillation and has a boiling point between 214° C. and 240° C./2 mm Hg.

It is an advantage of the present invention that a low cost by-product from the manufacture of 2,6-dimethylphenol, containing more than about 95% mesitol may be utilized to prepare a liquid mixed phosphate ester that remains liquid and may be pumped at room temperature.

The present invention will be further illustrated by the following patent examples.

EXAMPLE I

Eighty-two thousand and one hundred pounds (approximately 603 moles) of distilled still bottom phenols containing more than about 95 weight percent of mesitol, less than 2 weight percent of 2,4-xylenol, less than 0.5 weight percent 2,6-dimethyl phenol and no more than about 0.5 weight percent of total ortho monosubstituted phenol isomers were heated in a reactor with 650 pounds (4.87 moles) of aluminum chloride to a temperature of 120° C. The temperature of the distilled still bottom phenols was maintained between 120° C. and 130° C. while 78,530 pounds (512 moles) of phosphorus oxychloride was added with agitation over a period of 2½ hours. At the end of this time, gas chromatographic analysis indicated that less than 1% of free mesitol remained in the reaction mixture.

When analysis indicated that less than 1% of mesitol remained in the reaction mixture, 93,640 pounds (995 moles) of phenol was added with agitation to the reaction mixture over a period of 2 hours while maintaining the temperature between 120° C. and 130° C. The reaction was completed by raising the temperature of the reaction mixture from 120° C. to 130° C. to 220° C. and holding the temperature of the reaction mixture at 220° C. with agitation until two consecutive gas chromatograms indicated that there was no significant change in the composition. This required about 4 hours.

The crude reaction product, 196,120 pounds was then distilled to recover 19,900 pounds of volatile components; boiling at 45° C. to 70° C./1.6 mm Hg, and 165,000 pounds of the mixed phenyl/mesityl phosphate ester; boiling at 214° C. to 240° C./2 mm Hg. The still residue containing the aluminum chloride and high boiling products weighed 7,270 pounds.

A gas chromatogram of the mixed phenyl/mesityl phosphate ester collected at 214° C. to 240° C./2 mm Hg indicated the following composition:

| | |
|---|---|
| Triphenyl Phosphate | 20 weight percent |
| Diphenyl Mesityl Phosphate | 39.8 weight percent |
| Phenyl Dimesityl Phosphate | 40.2 weight percent |
| Trimesityl Phosphate | 0.0 weight percent |

This product contained 8.3% phosphorus, 0.02% moisture, 51.8 ppm of free phenol and had an acidity of 0.004% (determined as acetic acid), and a specific gravity of 1.181. The viscosity of this product (65.6° C.) was 0.000024 meter$^2$ per second (24 centistokes) and its color on the APHA scale (platinum-cobalt) was 50.

The product obtained by the method described in Example I above may deposit a small quantity of crystalline material upon standing for several months at room temperature. The crystalline material, however, remains in suspension so that the mixed aryl phosphate may be readily transferred by pumping.

EXAMPLE II

The phenyl/mesityl phosphate ester prepared as described in Example I above was evaluated as a flame retardant by dispersing 8 parts thereof throughout 100 parts of a 55 weight percent polyphenylene ether—45 weight percent high impact polystyrene resin. Mixing of the additive and resin is accomplished in a Brabender type mixer (HAAKE RHEOMIX MODEL 600 with REOCORD EU10 attachment, manufactured by Haake, Inc., 244 Saddle River Road, Saddle Brook, N.J. 07662). The mixing takes place at 265° C. at which temperature some of the additive is volatilized. The Underwriter Laboratories rating (Vertical Burn Test) for the various combinations tested is indicated in Table I.

In testing the polyphenylene ether-high impact polystyrene resin compositions containing a flame retardant additive, the flame retardant properties are determined following procedures established by the Underwriter Laboratories Bulletin No. 94, STANDARD FOR TESTS FOR FLAMMABILITY OF PLASTIC MATERIALS FOR PARTS IN DEVICES AND APPLICANCES; Second Edition, Second Impression (as revised to Feb. 1, 1974) dated July 30, 1976. The Vertical Burning Test for classifying Materials 94 V-0, 94 V-1 or 94 V-2 and described in Section 3 of this publication is used. In this test, the V-0 rating indicates the best flame resistance and the V-2 rating indicates the poorest flame resistance.

The effect of increasing the amount of the phenyl/mesityl phosphate ester on different polyphenylene oxide-polystyrene resin compositions is summarized in Table I.

TABLE I

| Resin[1] | FR[2] | OI[3] | UL-94[4] |
|---|---|---|---|
| A | 8 | 33.3 | V-2 |
| B | 8 | 31.0 | — |
| A | 12 | 34.8 | V-0 |
| B | 12 | 34.1 | V-1 |

[1]A = 55 weight percent polyphenylene ether
45 weight percent high impact polystyrene
B = 40 weight percent polyphenylene ether
32.7 weight percent ABS
27.3 weight percent polystyrene
[2]FR = parts per hundred of phenyl/mesityl ester fire retardant
[3]OI = Oxygen Index
[4]UL-94 = Underwriter Laboratory Flammability Test

I claim:
1. A mixed phosphate ester composition useful as a fire retardant additive, comprising about 20 weight percent triphenyl phosphate, about 40 weight percent diphenyl mesityl phosphate, about 40 weight percent phenyl dimesityl phosphate, said mixed ester composition having a viscosity at 65.6° C. no greater than about 0.000024 meter$^2$ per second and having a phosphorus analyses of from about 8.2% to about 8.4%.

2. A mixed phosphate ester composition useful as a fire retardant additive, comprising about 20 weight percent triphenyl phosphate, about 40 weight percent diphenyl mesityl phosphate, about 40 weight percent phenyl dimesityl phosphate, said mixed ester composition having a viscosity at 65.6° C. no greater than about 0.000024 meter$^2$ per second and having a phosphorus analyses of from about 8.2% to about 8.4%, made by:
   (a) heating from abut 1.02 to about 1.23 moles of distilled still bottom phenols containing more than 95 weight percent of mesitol, no more than about 2 weight percent 2,4-xylenol, and no more than about 0.5 weight percent of total 2-methyl phenol isomers in the presence of a Friedel-Crafts catalyst to a temperature of about 120° C. to 130° C. and adding with agitation about 1.0 mole of phosphorus oxychloride over a period of time to form a reaction mixture;
   (b) maintaining the temperature of the reaction mixture at 120° C. to 130° C. until the amount of unreacted mesitol is less than one weight percent of said distilled still bottom phenols;
   (c) adding to the reaction mixture with agitation over a period of time from about 1.9 to about 2.12 moles of phenol while continuing to maintain said reaction mixture at 120° C. to 130° C.;
   (d) heating said reaction mixture up to about 220° C. after addition of all of the phenol and maintaining said reaction mixture at that temperature with agitation for sufficient time to form a mixed phosphate ester composition; and
   (e) distilling said mixed phosphate ester composition and collecting a product boiling at about 214° C. to 240° C./2 mm Hg.

* * * * *